US006541631B1

(12) United States Patent
Zahr et al.

(10) Patent No.: US 6,541,631 B1
(45) Date of Patent: Apr. 1, 2003

(54) METHODS OF SEPARATING FTC ISOMERS AND DERIVATIVES THEREOF

(75) Inventors: Salah Zahr, Acton, MA (US); David A. Swanson, Burlington, MA (US); Adel M. Moussa, Burlington, MA (US); Luning Han, Allston, MA (US)

(73) Assignee: Pharma-Eco Laboratories, Inc., Devens, MA (US)

( * ) Notice: Subject to any disclaimer, the term of this patent is extended or adjusted under 35 U.S.C. 154(b) by 0 days.

(21) Appl. No.: 09/579,796

(22) Filed: May 26, 2000

Related U.S. Application Data

(60) Provisional application No. 60/136,009, filed on May 26, 1999.

(51) Int. Cl.⁷ .............................................. C07D 411/04
(52) U.S. Cl. ...................................................... 544/317
(58) Field of Search ......................................... 544/317

(56) References Cited

U.S. PATENT DOCUMENTS

| 5,000,794 A | 3/1991 | Kulprathipanja ............. 127/55 |
| 5,889,186 A | 3/1999 | Gattuso ....................... 564/304 |

FOREIGN PATENT DOCUMENTS

| EP | 0 382 526 | 8/1990 |
| WO | WO 92/18517 | 10/1992 |

OTHER PUBLICATIONS

Hawley, Gessner, "The Condensed Chemical Dictonary", 1977, Van Nostrand, New York, p. 823–4.*

Adachi, S., "Simulated moving–bed chromatography for continuous separation of two components and its application to bioreactors," *Jour. of Chromatography A* 658:271–282 (1994).

Pais, L.S. et al., "Separation of 1,1'–bi–2–naphthol enantiomers by continuous chromatography in simulated moving bed," *Chemical Engineering Science*, 52(2):245–257 (1997).

Nagamatsu, Shinji et al., "Optical resolution of a pharmaceutical intermediate by Simulated Moving Bed," *Chiral Europa* (1996).

Strube, J. et al, "Comparison of Batch Elution and Continuous Simulated Moving Bed Chromatography," *Organic Process Research and Development* 2:305–319 (1998).

* cited by examiner

Primary Examiner—Mukund J. Shah
Assistant Examiner—Thomas C McKenzie
(74) Attorney, Agent, or Firm—Hamilton, Brook, Smith & Reynolds, P.C.

(57) ABSTRACT

The present invention relates to a method of preparing enantiomers and diastereomers of a 2',3'-dideoxy-5-fluoro-3'thiocytadine (FTC) or a derivative thereof as represented by the following structural formula:

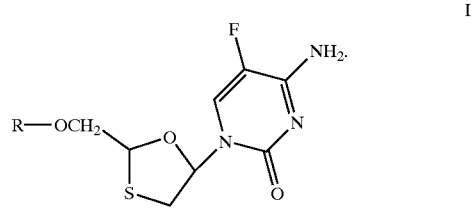

In Structural Formula I, R is H, a substituted or unsubstituted organic acid radical, a substituted or unsubstituted alkyl group, a substituted or unsubstituted aryl group, a substituted or unsubstituted heteroaryl group, a substituted or unsubstituted aralkyl group, a substituted or unsubstituted heteroaralkyl group, a substituted or unsubstituted cycloalkyl group, a substituted or unsubstituted heterocycloalkyl group, a substituted or unsubstituted cycloalkylalkyl, a substituted or unsubstituted heterocycloalkylalkyl, a sugar or a protecting group.

17 Claims, 4 Drawing Sheets

METHODS OF SEPARATING FTC ISOMERS AND DERIVATIVES THEREOF

RELATED APPLICATION

This application claims the benefit of U.S. Provisional Application No. 60/136,009, filed May 26, 1999, the entire teachings of which are incorporated herein by reference.

BACKGROUND OF THE INVENTION

A variety of methods have been utilized to obtain compounds in stereochemically pure form. While certain diastereomers and enantiomers can be synthesized using asymmetric synthetic techniques, not all compounds can be obtained in this manner. Moreover, such syntheses often require expensive reagents. Alternatively, diastereomers can be obtained by selective recrystallization of one diastereomer. In some instances, selective recrystallization can also be used to prepare an enantiomer. The enantiomer must first be converted to a diastereomer by reacting it with a chiral auxiliary, then one diastereomer can be selectively recrystallized. After recrystallization the chiral auxiliary is removed to give one enantiomer. Selective recrystallization, however, is not suitable for the preparation of all compounds. In addition, it is considered inefficient, in that product recovery is often low and purity uncertain.

Diastereomers can also be resolved chromatographically, although the large amount of solvent required for conventional preparative chromatography results in the preparation of relatively dilute products. Moreover, limited throughput makes conventional methods impractical for large-scale production. Enantiomers can also be separated chromatographically when a chiral solid support is used.

A very complex chromatography process, simulated moving bed chromatography (SMB), has been applied to the large-scale separation of C8 hydrocarbons (Broughton, D. B., *Chem. Eng Prog.* (1968), 68:6).; the separation of fructose and glucose by adsorption on a zeolite solid phase (Kieprathipanja, S., U.S. Pat. No. : 5,000,794); and also to the separation of enantiomers using a chiral solid support (Gattuso, M. J., et al., *Chemistry Today* (1996), 17 and Gattuso, M. J., U.S. Pat. No. : 5,889,186 (1999)). However, the effective application of simulated moving bed technology to the separation of any specific group of chemical compounds is quite unpredictable. This is particularly true when the compounds to be separated are closely related structurally and are intended for pharmaceutical use, as are the stereoisomers of 2',3'-dideoxy-5-fluoro-3' thiocytadines derivatives (hereinafter "FTC"). FTC derivatives, particularly the L or (−) enantiomer of cis-FTC alcohol, have been shown to exhibit therapeutic antiviral effects.

Thus, an effective method of preparing stereochemically pure compounds which are FTC derivatives would be very useful.

SUMMARY OF THE INVENTION

The present invention relates to a method of preparing a cis or a trans diastereomer of a 2',3'-dideoxy-5-fluoro-3' thiocytadine derivative represented by Structural Formula I:

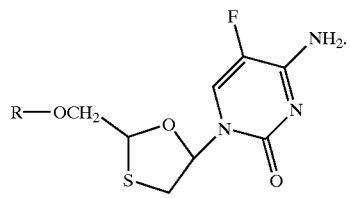

In Structural Formula I, R is H, a substituted or unsubstituted organic acid radical, a substituted or unsubstituted alkyl group, a substituted or unsubstituted aryl group, a substituted or unsubstituted heteroaryl group, a substituted or unsubstituted aralkyl group, a substituted or unsubstituted heteroaralkyl group, a substituted or unsubstituted cycloalkyl group, a substituted or unsubstituted heterocycloalkyl group, a substituted or unsubstituted cycloalkylalkyl, a substituted or unsubstituted heterocycloalkylalkyl, a sugar or a protecting group. The method involves forming a solution of the cis and the trans diastereomers of the 2',3'-dideoxy-5-fluoro-3' thiocytadine derivative, then separating the cis and the trans diastereomers of the 2',3'-dideoxy-5-fluoro-3' thiocytadine derivative by simulated moving bed chromatography to obtain at least one diastereomer. In one embodiment, the cis and the trans diastereomers of the 2',3'-dideoxy-5-fluoro-3' thiocytadine derivative are each recovered in at least 95% diastereomeric excess. In another embodiment, the cis diastereomer of the 2',3'-dideoxy-5-fluoro-3' thiocytadine derivative is recovered in at least 95% diastereomeric excess, and the trans diastereomer of the 2',3'-dideoxy-5-fluoro-3' thiocytadine derivative or a mixture containing the trans diastereomer of the 2',3'-dideoxy-5-fluoro-3' thiocytadine derivative is recovered.

In another embodiment, the invention relates to a method of preparing an enantiomer of a 5-fluoro-1-{2-(hydroxymethyl)-1,3-oxathiolan-5-yl}cytosine. The method involves reacting racemic 5-fluoro-1-{2-(hydroxymethyl)-1,3-oxathiolan-5-yl}cytosine with a chiral auxiliary to form a mixture of diastereomers represented by Structural Formula II:

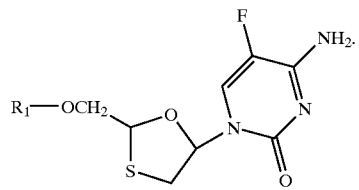

In Structural Formula II, $R_1$, is a chiral auxiliary. The mixture of diastereomers formed by reacting 5-fluoro-1-{2-(hydroxymethyl)-1,3-oxathiolan-5-yl}cytosine with a chiral auxiliary is separated by simulated moving bed chromatography to obtain at least one diastereomer. The chiral auxiliary is then removed from at least one diastereomer obtained by the simulated moving bed separation to form an enantiomer of a 5-fluoro-1-{2-(hydroxymethyl)-1,3-oxathiolan-5-yl}cytosine. In one embodiment, at least one of the diastereomers of the 2',3'-dideoxy-5-fluoro-3' thiocytadine derivative is recovered in at least 95% diastereomeric excess.

In another embodiment, the invention relates to a method of preparing an enantiomer of a cis-2',3'-dideoxy-5-fluoro-3' thiocytadine or a trans-2',3'-dideoxy-5-fluoro-3' thiocytadine derivative represented by Structural Formula I. The method involves forming a solution containing a first and a second enantiomer of the cis-2',3'-dideoxy-5-fluoro-3' thiocytadine derivative or a solution containing a first and a second enantiomer of the trans-2',3'-dideoxy-5-fluoro-3' thiocytadine derivative. The first and second enantiomer of the cis-2',3'-dideoxy-5-fluoro-3' thiocytadine derivative or the first and second enantiomer of the trans-2',3'-dideoxy-5-fluoro-3' thiocytadine derivative are then separated by simulated moving bed chromatography using a chiral solid support to obtain at least one of the enantiomers of the cis-2',3'-dideoxy-5-fluoro-3' thiocytadine derivative or at least one of the enantiomers of the trans-2',3'-dideoxy-5-fluoro-3' thiocytadine derivative.

In another embodiment, the invention relates to a method of preparing an enantiomer of cis-{5-(4-amino-5-fluoro-2-oxo-1(2H)-pyrimidinyl)-1,3-oxathiolan-2-yl}methyl butanoate represented by Structural Formula III:

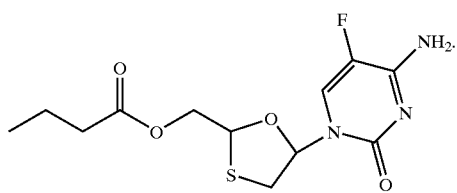

III

The method involves forming a solution containing a first and a second enantiomer of cis-{5-(4-amino-5-fluoro-2-oxo-1(2H)-pyrimidinyl)-1,3-oxathiolan-2-yl}methyl butanoate. The first and second enantiomer of cis-{5-(4-amino-5-fluoro-2-oxo-1(2H)-pyrimidinyl)-1,3-oxathiolan-2-yl}methyl butanoate are then separated by simulated moving bed chromatography using a chiral solid support to obtain at least one of the enantiomers of cis-{5-(4-amino-5-fluoro-2-oxo-1(2H)-pyrimidinyl)-1,3-oxathiolan-2-yl}methyl butanoate.

In another embodiment, the invention involves a method of preparing a cis-5-fluoro-1-{2-(hydroxymethyl)-1,3-oxathiolan-5-yl}cytosine enantiomer represented by Structural Formula IV:

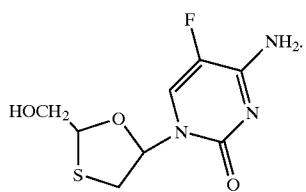

IV

The method involves forming a solution of a first and a second enantiomer of cis-5-fluoro-1-{2-(hydroxymethyl)-1,3-oxathiolan-5-yl}cytosine. The first and second enantiomer of cis-5-fluoro-1-{2-(hydroxymethyl)-1,3-oxathiolan-5-yl}cytosine are then separated by simulated moving bed chromatography using a chiral solid support to obtain at least one of the enantiomers of cis-5-fluoro-1-{2-(hydroxymethyl)-1,3-oxathiolan-5-yl}cytosine. Preferably, the enantiomer which is obtained is (−) cis-5-fluoro-1-{2-(hydroxymethyl)-1,3-oxathiolan-5-yl}cytosine.

When the method of the invention involves separating enantiomers of a 2',3'-dideoxy-5-fluoro-3' thiocytadine derivative by simulated moving bed chromatography, the method can further include a step of contacting the second enantiomer of the 2',3'-dideoxy-5-fluoro-3' thiocytadine derivative or a mixture containing the second enantiomer of the 2',3'-dideoxy-5-fluoro-3' thiocytadine derivative with a base to reform a mixture containing the first enantiomer of the 2',3'-dideoxy-5-fluoro-3' thiocytadine derivative and the second enantiomer of the 2',3'-dideoxy-5-fluoro-3' thiocytadine derivative. Suitable bases include sodium hydride, an alkyl lithium such as n-butyl lithium, potassium t-butoxide in dimethylsulfoxide, 1,8-diazabicyclo{5.4.0}undec-7-ene (hereinafter "DBU"), and lithium diisopropylamide (hereinafter "LDA"). The reformed mixture of the first and the second enantiomers of the 2',3'-dideoxy-5-fluoro-3' thiocytadine derivative are separated by simulated moving bed chromatography such that the first enantiomer 2',3'-dideoxy-5-fluoro-3' thiocytadine derivative is recovered in 95% enantiomeric excess, and the second enantiomer of the 2',3'-dideoxy-5-fluoro-3' thiocytadine derivative or a mixture containing the second enantiomer of the 2',3'-dideoxy-5-fluoro-3' thiocytadine derivative is recovered. In a preferred embodiment, the first enantiomer of 2',3'-dideoxy-5-fluoro-3' thiocytadine derivative is recovered from the reformed mixture in at least about 90% yield.

In contrast to selective recrystallization, more than one stereoisomer can be collected by the method of the invention in high diastereomeric or enantiomeric excess without additional processing steps. The methods of the invention also provide for reconverting, e.g., reracimizing, an undesired enantiomer into a racemic mixture which can be separated using simulated moving bed chromatography, and thus, greatly increasing the total recovery of a desired enantiomer.

The method of the invention results in an unexpectedly effective separation of stereoisomers of FTC derivatives, even those which exhibit relatively low solubilities in many common solvents. The parameters determined for the process result in an excellent degree of separation for stereoisomers of FTC derivatives. Moreover, the separation can be achieved within the range of retention times available to most simulated moving bed systems.

Moreover, due to the fact that the methods of the invention require far less solvent than conventional separations, they are particularly suited for large scale operations. This process advantage further results in the products obtained from simulated moving bed separation being more concentrated and containing less solvent than those obtained using standard chromatographic techniques. Not only do such products require less post-separation treatment, such as evaporation of excess solvent, they are particularly suited for use in pharmaceutical preparations.

DETAILED DESCRIPTION OF THE INVENTION

Figure 1:
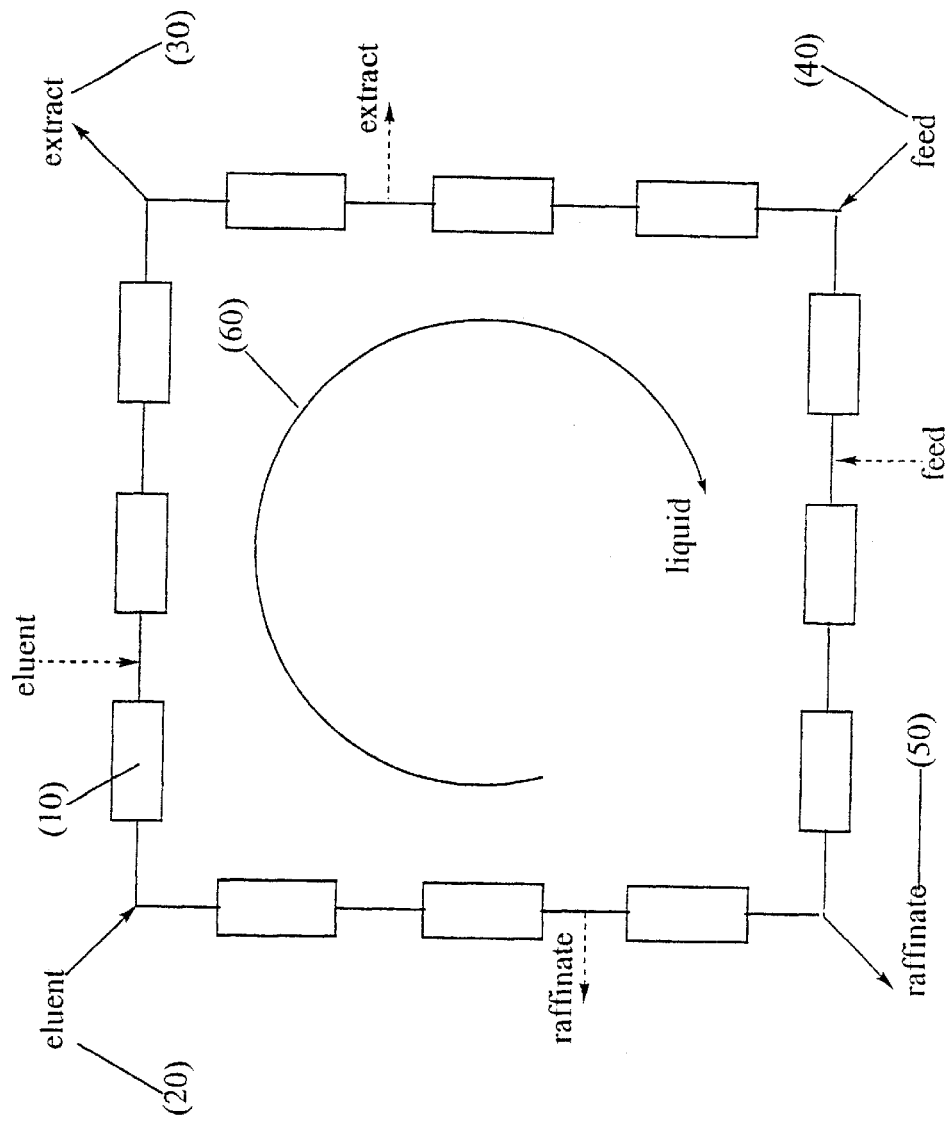
FIG. 1 is a schematic diagram of a simulated moving bed chromatographic system having twelve columns and suitable for use with the methods of the present invention.
Figure 2:
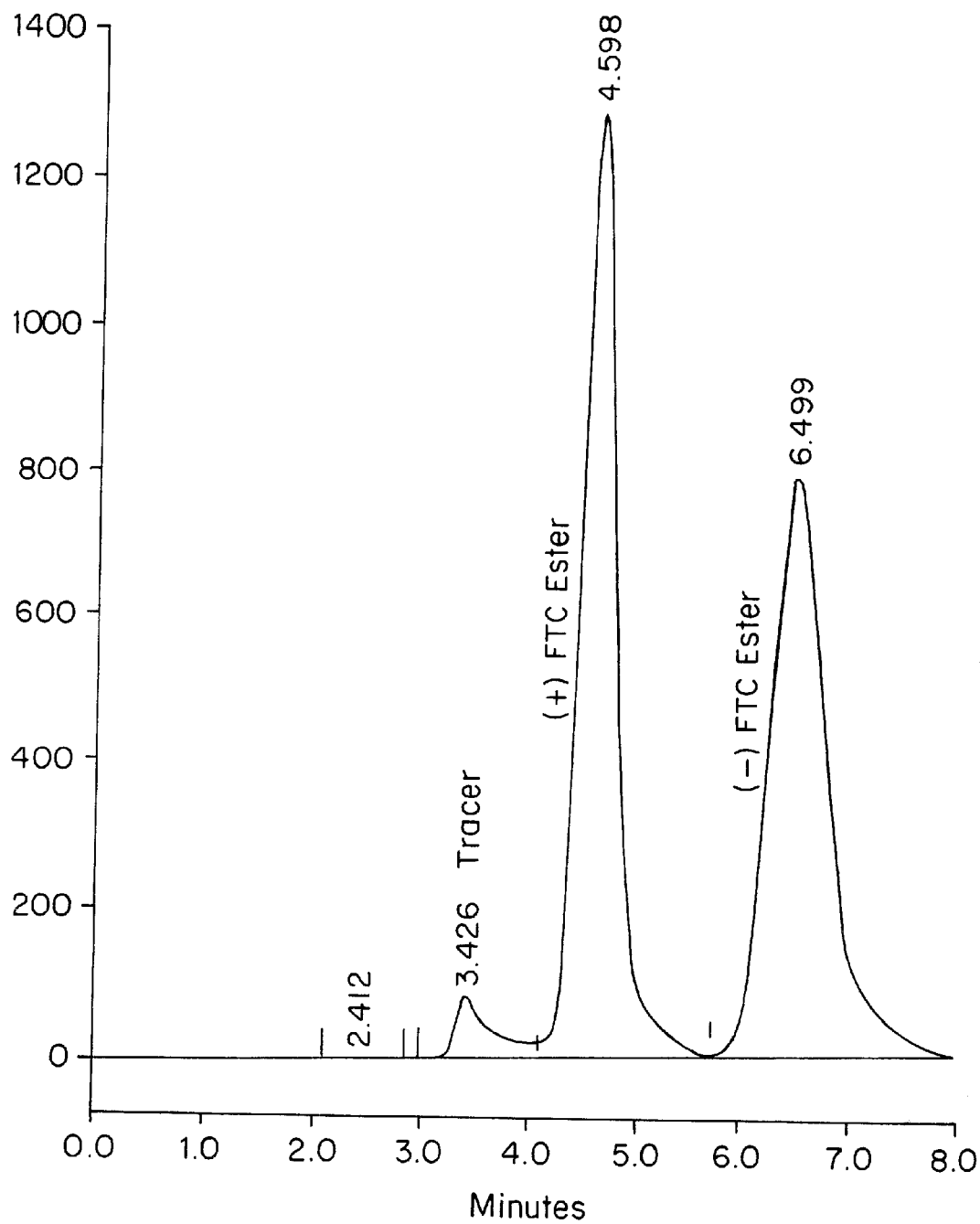
FIG. 2 is a chromatogram showing the separation of two enantiomers of an FTC ester according to a method of the invention.
Figure 3:
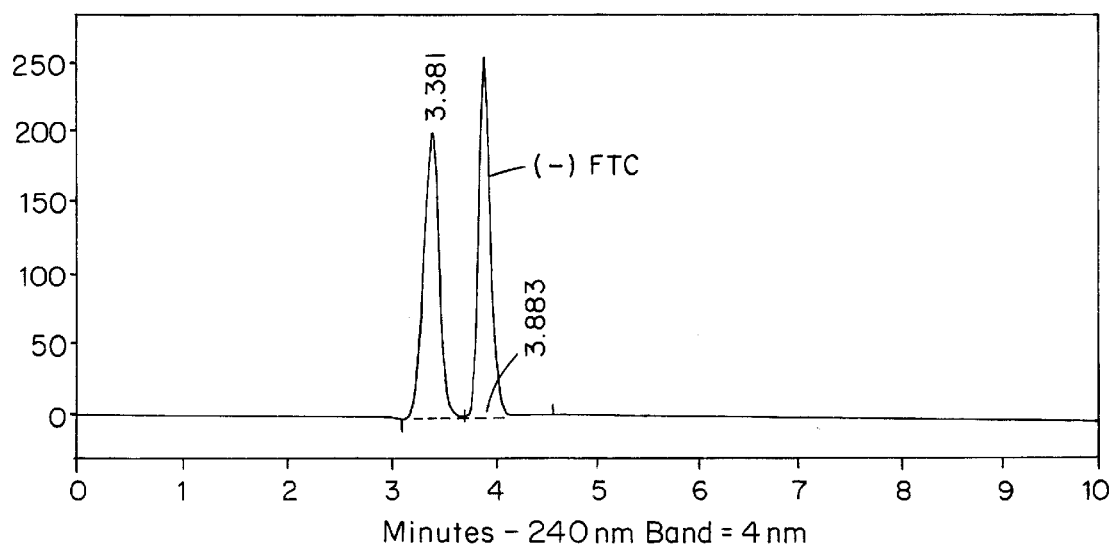
FIG. 3 is a chromatogram showing the separation of two enantiomers of an FTC alcohol according to a method of the invention.
Figure 4:
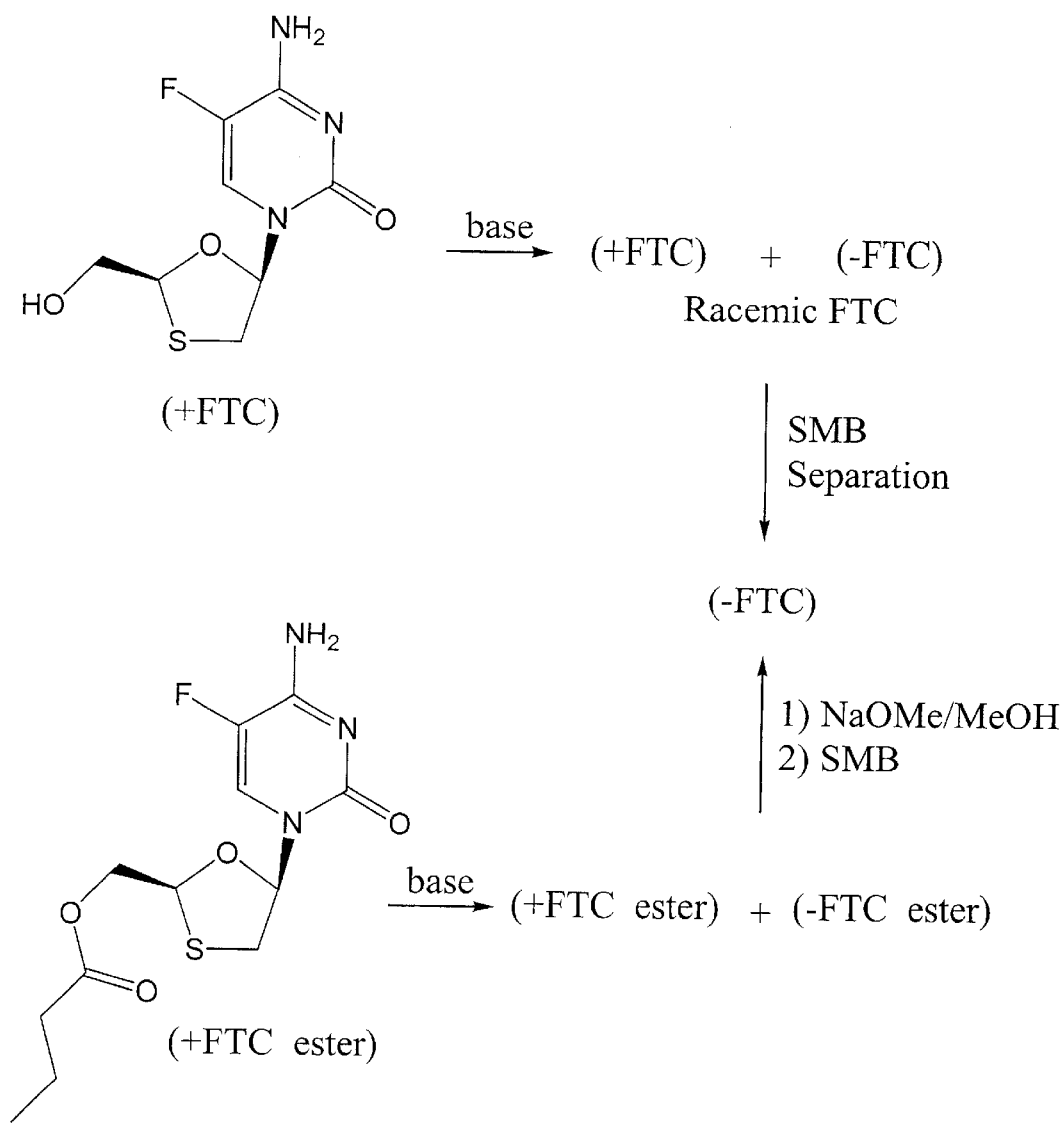
FIG. 4 illustrates a method of forming a reracimized solution.

The features and other details of the method of the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

As used herein, alkyl groups include straight chained or branched $C_{1-8}$ hydrocarbons which are completely saturated. Preferably, alkyl groups have from one to six carbon atoms.

Cycloalkyl groups, as used herein, include $C_{3-8}$ hydrocarbons which are completely saturated.

A cycloalkylalkyl, as used herein, is a cycloalkyl that is linked to a compound by an alkyl group having from one to about six carbon atoms.

An aryl group, as used herein, includes carbocyclic aromatic rings systems and carbocyclic aromatic ring systems which are fused to a carbocyclic non-aromatic ring (e.g., phenyl, naphthyl and tetrahydronaphthyl).

Heteroaryl groups, as used herein, include heteroaryl ring systems (e.g., thienyl, pyridyl, pyrazolyl, isoxazolyl, thiadiazolyl, oxadiazolyl, indazolyl, furyl, pyrrolyl, imidazolyl, pyrazolyl, triazolyl, pyrimidinyl, pyridazinyl, pyrazinyl, thiazolyl, isoxazolyl, isothiazolyl, tetrazolyl, or oxadiazolyl) and heteroaryl ring systems in which a carbocyclic aromatic ring, carbocyclic non-aromatic ring or heteroaryl ring is fused to one or more other heteroaryl rings (e.g., benzo(b)thienyl, benzimidazole, benoxazolyl, benzofuryl, benzothiazolyl, indolyl, indolizinyl, tetrahydroindolyl, azaindolyl, indazolyl, quinolyl, isoquinolyl, imidazopyridinyl, purinyl, and pyrrolo{2,3-d}pyrimidinyl, pyrazolo{3,4-d}pyrimidinyl).

An aralkyl group, as used herein, is an aryl that is linked to a compound by an alkyl group having from one to about six carbon atoms.

An heteroaralkyl group, as used herein, is a heteraryl that is linked to a compound by an alkyl group having from one to about six carbon atoms.

A heterocycloalkyl group, as used herein, is a non-aromatic ring system that has 3 to 9 atoms and includes at least one heteroatom, such as nitrogen, oxygen, or sulfur. Examples of heterocycloalkyl groups include piperazinyl, piperidinyl, homopiperazinyl, quinuclidinyl, azetidinyl, morpholinyl, thiomorpholinyl, and thiazolidinyl.

The term "heterocycloalkylalkyl," as used herein, is a heterocycloalkyl that is linked to a compound by an alkyl group having from one to about six carbon atoms.

The term "organic acid radical" is intended to encompass groups including an organic radical formed from an organic acid by removal of the hydroxy group. The following are representative of organic acid radicals

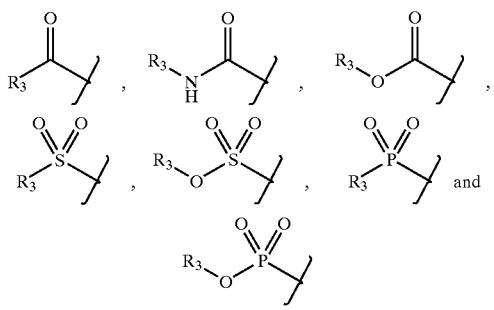

wherein, $R_3$ is H, an alkyl group, an aryl group, a heteroaryl group, an aralkyl group, a heteroaralkyl group, a cycloalkyl group, a heterocycloalkyl group, a cycloalkylalkyl, or a heterocycloalkylalkyl. The term "substituted organic acid radical," is an organic acid radical in which $R_3$ is substituted.

The term "sugar", as used herein, is intended to encompass monosaccharides and disaccharides. Monosaccharides can be either aldoses or ketonic sugars. Structural Formula V represents the straight-chain formula of an aldose sugar and Structural Formula VI represents the straight chain formula of a ketonic sugar.

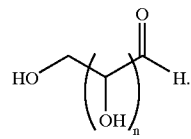

V

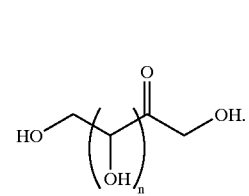

VI

In Structural Formulas V and VI, n is 4, 5 or 6. A disaccharide is a dimer of two monosaccharides.

The term "protecting group," as used herein, refers to alcoholic protecting groups which are described in Greene and Wuts, "Protective Groups in Organic Synthesis", John Wiley & Sons (1991), the entire teachings of which are incorporated by reference herein. The skilled artisan can select, using no more than routine experimentation, suitable protecting groups for use in the disclosed separation, including protecting groups other than those described below, as well as conditions for applying and removing the protecting groups.

Examples of suitable alcohol protecting groups include benzyl, allyl, trimethylsilyl, tert-butyldimethylsilyl, esters such as acetate, propanoate, butanoate and the like. Butanoate is a preferred alcohol protecting group.

The term "chiral auxiliary" means a group which includes at least one chiral center and has an absolute configuration. A chiral auxiliary can be added to an alcohol by reacting the alcohol with a chiral acid or chiral acid halide which has a (+) or (−) rotation of plane polarized light. Examples of chiral acids which can be used to form chiral auxiliaries include (+) or (−) tartaric acid, (+) or (−) di-p-toluoyltartaric acid, (+) or (−) di-o-toluoyltartaric acid, (+) or (−) O-methyl mandelic acid, and (+) or (−) camphor sulfonic acid. Examples of chiral acid halides include (+) or (−) tartaric chloride, (+) or (−) tartaric bromide, (+) or (−) di-p-toluoyltartaric chloride, (+) or (−) di-p-toluoyltartaric bromide, (+) or (−) di-o-toluoyltartaric chloride, (+) or (−) di-o-toluoyltartaric bromide, (+) or (−) O-methyl mandelic chloride, (+) or (−) O-methyl mandelic bromide, (+) or (−) camphor sulfonic chloride and (+) or (−) camphor sulfonic bromide. Methods for reacting a chiral acid with an alcohol to form a chiral auxiliary group and methods of removing the chiral auxiliary are known to those skilled in the art. (See Wilen et al., "Strategies in Optical Resolution," *Tetrahedron* (1977), 33:2725; Jacques et al., *Enantiomers, Racemates and Resolutions* (1981), Wiley, New York; Newman, *Optical Resolution Procedures for Chemical Compound* (1979–1984), Vol. 1–3, Optical Resolution Information Center, Manhattan College, Riverside, N.Y., all of the teachings of which are incorporated herein by reference in their entirety.)

An organic acid radical, an alkyl group, an aryl group, a heteroaryl group, an aralkyl group, a heteroaralkyl group, a cycloalkyl group, a heterocycloalkyl group, a cycloalkylalkyl, and a heterocycloalkylalkyl can be substituted with one or more substituents. Suitable substituents for an organic acid radical, an alkyl group, an aryl group, a heteroaryl group, an aralkyl group, a heteroaralkyl group, a cycloalkyl group, a heterocycloalkyl group, a cycloalkylalkyl, and a heterocycloalkylalkyl include a) a halogen; b) an alkyl; c) an alkyl substituted with one or more halogen; d) cyano; e) nitro; f) hydroxyl; g) —$NR_4R_5$, wherein $R_4$ and $R_5$ are each independently H, an alkyl or an aryl; h) —$OR_4$, wherein $R_4$ is optionally substituted with one or more halogen; i) —$SR_4$, wherein $R_4$ is optionally substituted with one or more halogen; j) —$C(O)R_4$; k) —$C(O)NR4R_5$; and l) —$C(O)OR_4$.

When diastereomers are separated by the method of the invention, the simulated moving bed chromatography can have a reverse phase solid support, a normal phase solid support, a chiral solid support or an ion-exchange solid support. When enantiomers are separated a chiral solid support must be used. Preferably, the simulated moving bed uses a mobile phase which includes methanol.

In one embodiment, the method further contains a step of converting the 2',3'-dideoxy-5-fluoro-3' thiocytadine derivative to an FTC alcohol. In alternate embodiments, the conversion step occurs prior to the separation step or after the separation step.

The present application is directed to various aspects related to the separation of 2',3'-dideoxy-5-fluoro-3' thiocytadine compounds. The chemical name "2',3'-dideoxy-5-fluoro-3' thiocytadine" and its acronym "FTC" are intended to encompass 2',3'-dideoxy-5-fluoro-3' thiocytadine compounds including those derivatives described in this application, whether such compounds and derivatives are contained within a racemic or diastereomeric mixture or are in stereochemically pure form. Throughout this application, the name "2',3'-dideoxy-5-fluoro-3' thiocytadine derivative" or the term "FTC derivative" are utilized for those compounds represented by structural Formula I and II. Similarly, the IUPAC name "cis-{5-(4-amino-5-fluoro-2-oxo-1(2H)-pyrimidinyl)-1,3-oxathiolan-2-yl}methyl butanoate" and the term "FTC ester" are utilized when referring to the specific FTC derivatives represented by Structural Formula III, while the IUPAC name "cis-5-fluoro-1-{2-(hydroxymethyl)-1,3-oxathiolan-5-yl}cytosine" and the term "FTC alcohol" are utilized when referring to the specific FTC derivatives represented by Structural Formula IV.

Simulated moving bed chromatography is similar in principal to counter-current chromatography. In conventional one-dimensional chromatography using a solid stationary phase and a liquid mobile phase, two compounds are separated based on their differing affinities for the solid phase. The compound with a higher affinity for the stationary solid phase will remain absorbed, thus stationary, longer than the compound with less affinity for the stationary phase. Since the compound with less affinity for the stationary phase remains for a longer period of time in the liquid mobile phase, it moves down the column and away from the other compound.

In counter-current chromatography, the solid phase is not stationary. Rather, it moves in the opposite direction from the liquid mobile phase. Thus, the flow rates of the solid and liquid phases can be configured so that the two compounds being separated migrate in opposite directions. If the mixture of the two compounds enters the column through a feed in the center of the column, each separated compound can be collected at an opposite end of the column, one through the extract line, which contains the less absorptive compound, and the other through the raffinate line, which contains the more absorptive compound. In counter-current chromatography, the column can be loaded more highly with sample to be separated than is possible in standard chromatography. Therefore, it is particularly applicable to large scale separations. In practice, however, actual movement of the solid phase is difficult to achieve without mixing the two compounds being separated.

In simulated moving bed chromatography, a number of columns (10) are connected in a continuous series (see FIG. 1). The flow of the solid phase is simulated by moving the eluent (20), extract (30), feed (40) and raffinate (50) lines one column forward in the direction of the fluid flow (60) at fixed intervals. This system allows for continuous feed of a mixture of compounds to be separated, as well as continuous elution of separated product. Simulated moving bed chromatography can also be used to separate more than two compounds. Simulated moving bed chromatography is described in great detail in U.S. Pat. No. 2,985,589, the entire teachings of which are incorporated by reference herein.

A feature of the present invention is the adjustment of simulated moving bed separation conditions to obtain at least one diastereomer or enantiomer of an FTC derivative in 95% diastereomeric or enantiomeric excess. For a pair of diastereomers, diastereomeric excess of diastereomer D1 in relation to diastereomer D2 can be calculated using Equation (1):

$$\% \text{ diastereomeric excess} = \frac{(D1-D2)}{(D1+D2)} \times 100 \qquad (1)$$

In Formula (1), D1 and D2 are relative amounts of each diastereomer. The relative amount of each diastereomer can be determined by HPLC, NMR or other techniques known to those skilled in the art. Similarly, for a pair of enantiomers, enantiomeric excess of enantiomer E1 in relation to enantiomer E2 can be calculated using Equation (2):

$$\% \text{ enantiomeric excess} = \frac{(E1-E2)}{(E1+E2)} \times 100 \qquad (2)$$

The relative amounts of E1 and E2 can be determined by chiral HPLC or by NMR in the presence of a chiral shift reagent.

Table III and Table VI provide representative parameters for use in the separation of the enantiomers of the FTC ester and FTC alcohol derivatives, respectively. Methanol is utilized as the mobile phase in each recommended set of parameters. It will be realized that other solvents which provide requisite solubility for any particular FTC derivative and which are compatible with columns used in the simulated moving bed separations can also be used. Examples of suitable solvents include acetonitrile, ethanol, 2-propanol, a mixture of ethyl acetate and heptane, and tetrahydrofuran (hereinafter "THF"). Similarly, the ordinarily skilled artisan, having studied the teachings contained in this application, is now fully able to prepare simulated moving bed systems using other columns and configurations with equivalent settings to separate FTC derivatives.

If desired, prior to separating the diastereomers or enantiomers of the FTC derivative, the mixture can be converted to a different FTC derivative. For example, an FTC ester can be hydrolyzed to an FTC alcohol prior to separation of the diastereomers or enantiomers.

After separating the diastereomer or enantiomer of the FTC derivative by simulated moving bed chromatography, one or more diastereomer or enantiomer is recovered in at least 95% diastereomeric or enantiomeric excess. In the case where two diastereomers or two enantiomers are separated, both can be recovered in 95% diastereomeric or enantiomeric excess.

If desired, after the diastereomers or enantiomers of the FTC derivative have been separated, the diastereomer or enantiomer can be converted to a different FTC derivative, while retaining optical purity. For example, an FTC ester can be hydrolyzed to an FTC alcohol prior to separation of the diastereomers or enantiomers. Hydrolysis using sodium methoxide as a catalyst is a preferred method of accomplishing this conversion, although other methods can be used.

When only one enantiomer is a desirable product, the desired enantiomer, designated the first enantiomer, can be recovered in 95% enantiomeric excess and a second enantiomer or a mixture containing the second enantiomer can be recovered and converted into the desired product. The recovered second enantiomer or solution containing the second enantiomer can be contacted with a base to reracemize the second enantiomer of a FTC derivative.

The FTC derivative is contacted with a base such that a solution of the first and the second enantiomer of the FTC derivative is formed that contains a higher enantiomer excess of the first enantiomer than was previously present. This solution can then be separated by simulated moving bed chromatography to obtain the desired enantiomer of the FTC derivative in at least 95% enantiomeric excess. This cycle of reracimization and separation can be repeated until the desired enantiomer of the FTC derivative has been obtained from the mixture in about 75%, 80% or 85% yield, preferably in about 90% yield. Alternatively, the cycle of reracemization and separation can be repeated until less than 25%, 20% or 15%, preferably 10%, even more preferably, less than 5% of the undesired enantiomer remains unconverted into the desired diastereomer.

EXAMPLES

Example 1

Determination of Simulated Moving Bed Separation Conditions for Separation of Enantiomers of cis-FTC Ester A. Solubility of FTC Ester In order to have a concentrated sample for loading on the simulated moving bed separation system, a high degree of solubility in the mobile phase to be used for the separation is desirable. Therefore, the solubility of the FTC ester in several solvent systems was determined. The results are presented in Table I.

TABLE I

Solubility of cis-FTC Ester in various solvent systems.

| Mobile Phase | Temperature | Solubility |
|---|---|---|
| 100% acetonitrile | RT | 1.41% |
| 100% acetonitrile | 40–45 C | 3.85% |
| 100% ethanol | RT, 40–45 C | 1.28% |

TABLE I-continued

Solubility of cis-FTC Ester in various solvent systems.

| Mobile Phase | Temperature | Solubility |
|---|---|---|
| 100% isopropyl alcohol | RT, 40–45° C. | 0.38% |
| 20% isopropyl alcohol/80% water | 40–45° C. | 3.59% |
| 80% water/10% 2-propanol/10% butanol | 20° C. | 2.27% |
| 80% water/10% 2-propanol/10% butanol | 35° C. | 5.94% |
| 74.6% water/13.99% 2-propanol/11.41% butanol | 20° C. | 3.16% |
| 74.6% water/13.99% 2-propanol/11.41% butanol | 35° C. | 10.5% |
| 80% water/5.5% 2-propanol/14.5% butanol | 20° C. | 2.55% |
| 80% water/15% 2-propanol/5% butanol | 20° C. | 2.57% |
| 100% 2-propanol | 35° C. | 2.68% |
| 80% water/20% 2-propanol | 20° C. | 1.60% |
| 80% water/20% 2-propanol | 35° C. | 3.80% |
| 70% water/30% 2-propanol | 20° C. | 2.40% |
| 70% water/30% 2-propanol | 35° C. | 5.39% |
| 85% water/15% 2-propanol | 35° C. | 0.70% |
| 100% ethyl acetate | 20° C. | 3.03%?? |
| 100% acetonitrile | 50° C. | 6.20% |
| 95% water/5% dimethylformamide | 20° C. | 0.47% |
| 90% water/10% dimethylformamide | 20° C. | 1.13% |
| 85% water/15% dimethylformamide | 20° C. | 1.24% |
| 100% ethanol | 20° C. | 4.36% |
| 100% methanol | 20° C. | 11.73% |
| 50% ethanol/50% methanol | 20° C. | 9.03% |
| 90% water/10% ethylene glycol | 20° C. | N/A |
| 80% water/20% ethanol | 20° C. | 0.52% |
| 80% water/20% methanol | 20° C. | 0.81% |
| 85% water/10% 2-propanol/5% tetrahydrofuran | 20° C. | 0.64% |
| 80% water/15% 2-propanol/5% tetrahydrofuran | 20° C. | 0.89% |
| 80% water/20% tetrahydrofuran | 20° C. | 1.80% |
| 80% water/20% 2-butanol | 20° C. | 3.00% |

B. Separation of Enantiomers cis-FTC Ester Using Conventional One-Dimensional High Pressure Chromatography (HPLC)

Enantiomers were separated using a chiral solid support. The solvent front was determined by measuring the void time using standard chromatographic techniques. For example,1,3,5 tri-tert-butyl benzene was used as a tracer compound which eluted with the solvent front from the chiral compound. The capacity factors, $k_1'$ and $k_2'$ for each of the two ester enantiomers was determined for each column and mobile phase system using Equation (3):

$$k' = \frac{\text{(retention time)} - \text{(solvent front)}}{\text{(solvent front)}} \quad (3)$$

The selectivity constant, $\alpha$, for the system was calculated by taking the ratio of $k_2'$ to $k_1'$. A value of $\alpha$ of 1.15 or greater is necessary in order for separation of the enantiomers via simulated moving bed chromatography to be possible.

| Column Type | Length (mm) | Diameter (mm) | Particle size (μm) | Flow Rate (mL/min.) | Mobile Phase | $k_2'$ | α |
|---|---|---|---|---|---|---|---|
| Chirobiotic T | 250 | 4.6 | 10 | 1 | 50% methanol/50% THF | 4.33 | 1.70 |
| Chirobiotic V | 250 | 4.6 | 10 | 1 | 100% ethanol | 3.2 | 1.54 |
| Chirobiotic T | 250 | 4.6 | 10 | 1 | 90% methanol/10% DMF | 1.27 | 1.45 |
| Chiro- | 250 | 4.6 | 10 | 1 | 50% | 1.80 | 1.34 |

-continued

| Column Type | Length (mm) | Diameter (mm) | Particle size (μm) | Flow Rate (mL/min.) | Mobile Phase | $k_2'$ | α |
|---|---|---|---|---|---|---|---|
| biotic V | | | | | ethanol/ 50% methanol | | |
| Chirobiotic V | 250 | 4.6 | 10 | 1 | 100% methanol | 0.92 | 1.24 |
| Chiralpak AD | 250 | 4.6 | 5 | 1 | 100% methanol | 0.623 | 2.0 |

Table II: Separation of cis-FTC Ester Enantiomers.

Example 2

Separation of FTC cis-Ester Enantiomers Using Simulated Moving Bed Chromatography The SMB-L System was used to separate cis-FTC ester enantiomers using an eight column configuration. The columns used were Chiralpak AD columns (Daicel Chemical Industries, Ltd., Leicestershire, UK) (length 6.5 cm, diameter 1.0 cm, particle size 50 μm), which have a chiral solid support. The mobile phase used was 100% methanol. A solution of the enantiomers was fed onto the simulated moving bed columns at a rate of 1.03 mL/min. The extract rate was 6.80 mL/min., the total mobile phase rate was 33.08 mL/min., the fresh mobile phase rate was 7.88 mL/min., the raffinate flow rate was 2.10 mL/min., and the recycling flow rate was 25.20 mL/min. The cycle time was 8 minutes. Representative simulated moving bed separation conditions for separation of FTC Ester enantiomers are summarized in Table III.

| | |
|---|---|
| Column Diameter | 1.0 cm |
| Column Length | 25.0 cm |
| Number of Columns | 8 |
| Cycle Time | 8 min. |
| Dilute Feed Rate | 1.03 mL/min. |
| Total Mobile Phase Rate | 33.08 mL/min. |
| Extract Rate | 6.80 mL/min. |
| Raffinate Rate | 2.10 mL/min. |
| Recycle Mobile Phase Rate | 25.20 mL/min. |
| Fresh Mobile Phase Rate | 7.88 mL/min. |
| % of Feed in Mobile Phase | 15% |

Table III: Representative Parameters for Simulated Moving Bed Separation of cis-FTC Ester Enantiomers.

Example 3

Determination of Simulated Moving Bed Separation Conditions for Separation of Enantiomers of the cis-FTC Alcohol A. Solubility of FTC Alcohol In order to have a concentrated sample for loading on the simulated moving bed separation system, a high degree of solubility in the mobile phase to be used for the separation is desirable. Therefore, the solubility of the cis-FTC Alcohol in several solvent systems was determined. The results are presented in Table IV.

TABLE IV

Solubility of cis-FTC Alcohol in various solvent systems.

| Mobile Phase | Temperature | Solubility |
|---|---|---|
| 100% ethanol | RT | 0.51% |
| 100% methanol | RT | 0.77% |
| 100% methanol | 40–45° C. | 3.21% |
| 100% acetonitrile | RT | 0.38% |
| 100% isopropyl alcohol | RT | 0.38% |
| 100% water | RT | 0.37% |

B. Separation of cis-FTC Alcohol Enantiomers Using Conventional One-Dimensional High Pressure Chromatography (HPLC)

Enantiomers were separated using a chiral solid support. The solvent front was determined by measuring the void time using standard chromatographic techniques. For example,1,3,5 tri-tert-butyl benzene was used as a tracer compound which eluted with the solvent front from the chiral compound. The capacity factors, $k_1'$ and $k_2'$ for each of the two alcohol enantiomers was determined for each column and mobile phase system using Equation (3). The selectivity constant, a, for the system was calculated by taking the ratio of $k_2'$ to $k_1'$. A value of α of 1.15 or greater is necessary in order for separation of the enantiomers via simulated moving bed chromatography to be possible.

| Column Type | Length (mm) | Diameter (mm) | Particle size (μm) | Flow Rate (mL/min.) | Mobile Phase | $k_2'$ | α |
|---|---|---|---|---|---|---|---|
| Chiralpak AS | 250 | 4.6 | 5 | 1 | 100% isopropyl alcohol | 1.43 | 2.68 |
| Chiralpak AS | 250 | 4.6 | 5 | 1 | 100% ethanol | 0.86 | 3.0 |
| Chirobiotic V | 250 | 4.6 | 10 | 1 | 100% ethanol | 3.87 | 1.41 |
| Chirobiotic T | 250 | 4.6 | 10 | 2 | 90% methanol/ 10% 1% TEAA | 7.33 | 1.38 |
| Chiralpak AS | 250 | 4.6 | 5 | 1 | 50% ethanol/ 50% hexane | 1.080 | 2.12 |
| Chiralpak AS | 250 | 4.6 | 5 | 1 | 70% IPA/ 30% hexane | 1.64 | 2.45 |

Table V: Separation of cis-FTC Alcohol Enantiomers.

Example 4

Separation of cis-FTC Alcohol Enantiomers Using Chiral Simulated Moving Bed Chromatography The SMB-L System was used to separate cis-FTC alcohol enantiomers using an eight column configuration. The columns used were Chiralpak AD columns (Daicel Chemical Industries, Ltd., Leicestershire, UK) (length 25.0 cm, diameter 1.0 cm, particle size 50 μm), which have a chiral solid support. The mobile phase used was 100% methanol. A solution of the enantiomers was fed onto the simulated moving bed columns at a rate of 2.24 mL/min. The extract rate was 8.44 mL/min., the total mobile phase rate was 24.00 mL/min., the fresh mobile phase rate was 9.00 mL/min., the raffinate flow rate was 2.80 mL/min., and the recycling flow rate was 15.00 mL/min. The cycle time was 8 minutes. Representative simulated moving bed separation conditions for separation of FTC Alcohol enantiomers are summarized in Table VI.

| Column Diameter | 1.0 cm |
|---|---|
| Column Length | 25.0 cm |
| Number of Columns | 8 |
| Cycle Time | 8 min. |
| Dilute Feed Rate | 2.24 mL/min. |
| Total Mobile Phase Flow Rate | 24.00 mL/min. |
| Extract Flow Rate | 8.44 mL/min. |
| Raffinate Rate | 2.80 mL/min. |
| Recycling Flow Rate | 15.00 mL/min. |
| Fresh Mobile Phase Flow Rate | 9.00 mL/min. |
| % of Feed in Mobile Phase | 6.9% |

Table VI: Representative Parameters for Simulated Moving Bed Separation of cis-FTC Alcohol Enantiomers.

Example 5

Production of FTC Alcohol From FTC Ester

A 2L Erlenmeyer flask was purged with argon and 165.9 g (1 equivalent) of FTC ester was added. Then,1.4 L methanol and 128 g Dowex resin were added, respectively. The mixture was initially a slurry, then a clear brown solution. The mixture was stirred at room temperature for 3.5 hours. Thin layer chromatographic analysis showed that no starting material remained.

The Dowex resin was filtered out, and washed with 300 mL methanol. The filtrate was evaporated to yield a light brown solid. The light brown solid was treated with 300 mL methylene chloride. The suspension formed was stirred at room temperature for 1 hour, and filtered. The solid product was dried, about 90 g was produced. NMR analysis demonstrated that the product was FTC Alcohol.

Example 6

Production of FTC Alcohol From FTC Ester 4.0 mg of sodium methoxide was placed in a 100 mL round bottom flask, and anhydrous methanol was added immediately. FTC ester in the amount of 4.7 g (1 equivalent) was added in two portions. The initial suspension became brown clear solution after stirring at room temperature for a while. After 1 hour of stirring at room temperature, thin layer chromatography was performed on the sample. It showed both starting FTC ester and product FTC alcohol.

The reaction mixture was then stirred overnight. After overnight stirring, the clear solution became a suspension again. Thin layer chromatography of the reaction mixture showed the completion of the reaction. The methanol was removed from the reaction mixture. An NMR of the product, in dimethylsulfoxide, showed very clean product-FTC alcohol.

EQUIVALENTS

While this invention has been particularly shown and described with references to preferred embodiments thereof, it will be understood by those skilled in the art that various changes in form and details may be made therein without departing from the scope of the invention encompassed by the appended claims. The teachings of all applications, patents and other references cited herein are incorporated by reference in their entireties.

What is claimed is:

1. A method of preparing an enantiomer of cis-{5-(4-amino-5-fluoro-2-oxo-1(2H)-pyrimidinyl)-1,3-oxathiolan-2-yl}methyl butanoate represented by the following structural formula:

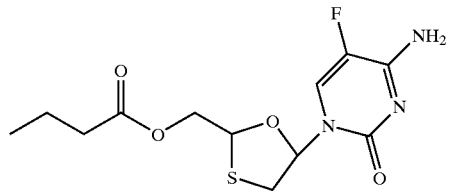

comprising the steps of:
 a) forming a solution containing a first and a second enantiomer of cis-{5-(4-amino-5-fluoro-2-oxo-1(2H)-pyrimidinyl)-1,3-oxathiolan-2-yl}methyl butanoate; and
 b) separating the first and second enantiomer of cis-{5-(4-amino-5-fluoro-2-oxo-1(2H)-pyrimidinyl)-1,3-oxathiolan-2-yl}methyl butanoate by simulated moving bed chromatography using a chiral solid support to obtain at least one of the enantiomers of cis-{5-(4-amino-5-fluoro-2-oxo-1(2H)-pyrimidinyl)-1,3-oxathiolan-2-yl}methyl butanoate.

2. The method of claim 1, wherein the simulated moving bed has a mobile phase which comprises methanol.

3. The method of claim 1, further comprising a step of converting the cis-{5-(4-amino-5-fluoro-2-oxo-1(2H)-pyrimidinyl)-1,3-oxathiolan-2-yl}methyl butanoate to a cis-5-fluoro-1-{2-(hydroxymethyl)-1,3-oxathiolan-5-yl}cytosine.

4. The method of claim 3, wherein the conversion step occurs prior to the separation step.

5. The method of claim 3, wherein the conversion step occurs after the separation step.

6. The method of claim 3, wherein the conversion results from a hydrolysis reaction.

7. The method of claim 1, wherein the first and the second enantiomer of cis-{5-(4-amino-5-fluoro-2-oxo-1(2H)-pyrimidinyl)-1,3-oxathiolan-2-yl}methyl butanoate are each recovered in at least 95% enantiomeric excess.

8. The method of claim 7, wherein the first enantiomer of cis-{5-(4-amino-5-fluoro-2-oxo-1(2H)-pyrimidinyl)-1,3-oxathiolan-2-yl}methyl butanoate is recovered in at least 95% enantiomeric excess, and the second enantiomer of cis-{5-(4-amino-5-fluoro-2-oxo-1(2H)-pyrimidinyl)-1,3-oxathiolan-2-yl}methyl butanoate or a mixture containing the second enantiomer of cis-{5-(4-amino-5-fluoro-2-oxo-1(2H)-pyrimidinyl)-1,3-oxathiolan-2-yl}methyl butanoate is recovered.

9. The method of claim 1, further comprising the steps of:
 a) contacting the second enantiomer of cis-{5-(4-amino-5-fluoro-2-oxo-1(2H)-pyrimidinyl)-1,3-oxathiolan-2-yl}methyl butanoate or a mixture containing the second enantiomer of cis-{5-(4-amino-5-fluoro-2-oxo-1(2H)-pyrimidinyl)-1,3-oxathiolan-2-yl}methyl butanoate with a base to reform a solution containing the first enantiomer of cis-{5-(4-amino-5-fluoro-2-oxo-1(2H)-pyrimidinyl)-1,3-oxathiolan-2-yl}methyl butanoate and the second enantiomer of cis-{5-(4-amino-5-fluoro-2-oxo-1(2H)-pyrimidinyl)-1,3-oxathiolan-2-yl}methyl butanoate; and
 b) separating the reformed first and second enantiomers of cis-{5-(4-amino-5-fluoro-2-oxo-1(2H)-pyrimidinyl)-1, 3-oxathiolan-2-yl}methyl butanoate by simulated moving bed chromatography using a chiral solid support such that the first enantiomer of cis-{5-(4-amino-5-fluoro-2-oxo-1(2H)-pyrimidinyl)-1,3-oxathiolan-2-yl}methyl butanoate is recovered in 95% enantiomeric excess, and the second enantiomer of cis-{5-(4-amino-5-fluoro-2-oxo-1(2H)-pyrimidinyl)-1,3-oxathiolan-2-yl}methyl butanoate or a mixture containing the second enantiomer of cis-{5-(4-amino-5-fluoro-2-oxo-1(2H)-pyrimidinyl)-1,3-oxathiolan-2-yl}methyl butanoate is recovered.

10. The method of claim 9, wherein the first enantiomer of cis-{5-(4-amino-5-fluoro-2-oxo-1(2H)-pyrimidinyl)-1,3-oxathiolan-2-yl}methyl butanoate is recovered from the reformed mixture in at least about 90% yield.

11. A method of preparing a cis-5-fluoro-1-{2-(hydroxymethyl)-1,3-oxathiolan-5-yl}cytosine enantiomer represented by the following structural formula:

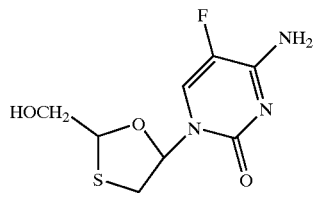

comprising the steps of:
   a) forming a solution of a first and a second enantiomer of cis-5-fluoro-1-{2-(hydroxymethyl)-1,3-oxathiolan-5-yl}cytosine; and
   b) separating the first and second enantiomer of cis-5-fluoro-1-{2-(hydroxymethyl)-1,3-oxathiolan-5-yl}cytosine by simulated moving bed chromatography using a chiral solid support to obtain at least one enantiomer of cis-5-fluoro-1-{2-(hydroxymethyl)-1,3-oxathiolan-5-yl}cytosine.

12. The method of claim 11, wherein the simulated moving bed has a mobile phase which comprises methanol.

13. The method of claim 12, wherein the first and the second enantiomer of cis-5-fluoro-1-{2-(hydroxymethyl)-1, 3-oxathiolan-5-yl}cytosine are each recovered in at least 95% enantiomeric excess.

14. The method of claim 11, wherein the first enantiomer of cis-5-fluoro-1-{2-(hydroxymethyl)-1,3-oxathiolan-5-yl}cytosine is recovered in at least 95% enantiomeric excess, and the second enantiomer of cis-5-fluoro-1-{2-(hydroxymethyl)-1,3-oxathiolan-5-yl}cytosine or a mixture containing the second enantiomer of cis-5-fluoro-1-{2-(hydroxymethyl)-1,3-oxathiolan-5-yl}cytosine is recovered.

15. The method of claim 11, wherein the first enantiomer of cis-5-fluoro-1-{2-(hydroxymethyl)-1,3-oxathiolan-5-yl}cytosine is (–) cis-5-fluoro-1-{2-(hydroxymethyl)-1,3-oxathiolan-5-yl}cytosine.

16. The method of claim 11, further comprising the steps of:
   a) contacting the second enantiomer of cis-5-fluoro-1-{2-(hydroxymethyl)-1,3-oxathiolan-5-yl}cytosine or a mixture containing the second enantiomer of cis-5-fluoro-1-{2-(hydroxymethyl)-1,3-oxathiolan-5-yl}cytosine with a base to reform a solution containing a first and a second enantiomer of cis-5-fluoro-1-{2-(hydroxymethyl)-1,3-oxathiolan-5-yl}cytosine; and
   b) separating the reformed first and second enantiomers of cis-5-fluoro-1-{2-(hydroxymethyl)-1,3-oxathiolan-5-yl}cytosine by simulated moving bed chromatography using a chiral solid support such that the first enantiomer of cis-5-fluoro-1-{2-(hydroxymethyl)-1,3-oxathiolan-5-yl}cytosine is recovered in 95% enantiomeric excess, and the second enantiomer of cis-5-fluoro-1-{2-(hydroxymethyl)-1,3-oxathiolan-5-yl}cytosine or a mixture containing the second enantiomer of cis-5-fluoro-1-{2-(hydroxymethyl)-1,3-oxathiolan-5-yl}cytosine is recovered.

17. The method of claim 16, wherein the first enantiomer of cis-5-fluoro-1-{2-(hydroxymethyl)-1,3-oxathiolan-5-yl}cytosine is recovered from the reformed mixture in at least about 90% yield.

* * * * *

UNITED STATES PATENT AND TRADEMARK OFFICE
CERTIFICATE OF CORRECTION

PATENT NO. : 6,541,631 B1
DATED : April 1, 2003
INVENTOR(S) : Salah Zahr et al.

It is certified that error appears in the above-identified patent and that said Letters Patent is hereby corrected as shown below:

Title page,
Item [73], Assignee, please delete "Pharma-Eco Laboratories, Inc., Devens, MA (US)" and insert -- Johnson Matthey Pharmaceutical Materials, Inc., Devens, MA (US) --.

Signed and Sealed this

Twenty-sixth Day of August, 2003

JAMES E. ROGAN
*Director of the United States Patent and Trademark Office*